(12) United States Patent
Gross

(10) Patent No.: US 8,980,344 B2
(45) Date of Patent: Mar. 17, 2015

(54) SKIN CARE PRODUCTS CONTAINING MULTIPLE ENHANCERS

(76) Inventor: Dennis F. Gross, New York, NY (US)

( * ) Notice: Subject to any disclaimer, the term of this patent is extended or adjusted under 35 U.S.C. 154(b) by 1182 days.

(21) Appl. No.: 12/243,665

(22) Filed: Oct. 1, 2008

(65) Prior Publication Data

US 2009/0117061 A1 May 7, 2009

Related U.S. Application Data

(60) Provisional application No. 60/976,792, filed on Oct. 1, 2007.

(51) Int. Cl.

| | |
|---|---|
| A61K 8/362 | (2006.01) |
| A61K 8/365 | (2006.01) |
| A61K 8/97 | (2006.01) |
| A61Q 19/00 | (2006.01) |
| A61K 8/19 | (2006.01) |
| A61K 8/26 | (2006.01) |
| A61K 8/27 | (2006.01) |
| A61K 8/31 | (2006.01) |
| A61K 8/34 | (2006.01) |
| A61K 8/368 | (2006.01) |
| A61K 8/37 | (2006.01) |
| A61K 8/39 | (2006.01) |
| A61K 8/40 | (2006.01) |
| A61K 8/44 | (2006.01) |
| A61K 8/46 | (2006.01) |
| A61K 8/49 | (2006.01) |
| A61K 8/55 | (2006.01) |
| A61K 8/60 | (2006.01) |
| A61K 8/63 | (2006.01) |
| A61K 8/64 | (2006.01) |
| A61K 8/66 | (2006.01) |
| A61K 8/67 | (2006.01) |
| A61K 8/73 | (2006.01) |
| A61K 8/92 | (2006.01) |
| A61K 8/96 | (2006.01) |
| A61K 8/98 | (2006.01) |
| A61Q 17/04 | (2006.01) |
| A61Q 19/02 | (2006.01) |
| A61Q 19/08 | (2006.01) |

(52) U.S. Cl.
CPC . *A61Q 19/00* (2013.01); *A61K 8/19* (2013.01); *A61K 8/26* (2013.01); *A61K 8/27* (2013.01); *A61K 8/31* (2013.01); *A61K 8/345* (2013.01); *A61K 8/365* (2013.01); *A61K 8/368* (2013.01); *A61K 8/37* (2013.01); *A61K 8/375* (2013.01); *A61K 8/39* (2013.01); *A61K 8/40* (2013.01); *A61K 8/44* (2013.01); *A61K 8/442* (2013.01); *A61K 8/466* (2013.01); *A61K 8/4913* (2013.01); *A61K 8/4926* (2013.01); *A61K 8/4946* (2013.01); *A61K 8/4953* (2013.01); *A61K 8/4973* (2013.01); *A61K 8/498* (2013.01); *A61K 8/55* (2013.01); *A61K 8/602* (2013.01); *A61K 8/63* (2013.01); *A61K 8/64* (2013.01); *A61K 8/66* (2013.01); *A61K 8/676* (2013.01); *A61K 8/73* (2013.01); *A61K 8/738* (2013.01); *A61K 8/922* (2013.01); *A61K 8/965* (2013.01); *A61K 8/97* (2013.01); *A61K 8/987* (2013.01); *A61Q 17/04* (2013.01); *A61Q 19/02* (2013.01); *A61Q 19/08* (2013.01)

USPC ............ 424/777; 424/773; 514/574; 514/557

(58) Field of Classification Search
CPC .......... A61K 8/362; A61K 8/97; A61K 8/365
See application file for complete search history.

(56) References Cited

U.S. PATENT DOCUMENTS

| | | | |
|---|---|---|---|
| 5,980,904 A * | 11/1999 | Leverett et al. | 424/725 |
| 6,403,110 B1 | 6/2002 | Siddiqui et al. | |
| 2003/0026820 A1* | 2/2003 | De Lacharriere et al. | 424/401 |
| 2006/0018867 A1* | 1/2006 | Kawasaki et al. | 424/70.122 |
| 2006/0093634 A1* | 5/2006 | Lutz et al. | 424/401 |
| 2007/0042920 A1 | 2/2007 | Schmit et al. | |
| 2008/0241084 A1* | 10/2008 | Siddiqui | 424/62 |

FOREIGN PATENT DOCUMENTS

| | | |
|---|---|---|
| DE | 102005019202 A1 | 10/2006 |
| FR | 2905596 A1 | 3/2008 |
| JP | -06321762 * | 11/1994 |
| JP | 2003201228 A * | 7/2003 ............... A61K 7/48 |
| WO | 95/13047 A1 | 5/1995 |
| WO | 98/56345 A1 | 12/1998 |
| WO | 2006/015675 A1 | 2/2006 |
| WO | 2006/048671 A1 | 5/2006 |
| WO | 2008/121315 A2 | 10/2008 |

OTHER PUBLICATIONS

International Search Report in PCT/US2008/078463 and Written Opinion, (Jun. 3, 2009).
C. Druckman, "Dangerous When Wet," The New York Times Magazine, www.nytimes.com, Feb. 5, 2006.

* cited by examiner

*Primary Examiner* — Abigail Fisher
*Assistant Examiner* — Jessica Kassa
(74) *Attorney, Agent, or Firm* — Kenyon & Kenyon LLP

(57) ABSTRACT

The present invention provides a skin care product comprising at least two enhancers and at least one skin care ingredient, wherein the at least two enhancers are selected from cyclodextrin, pentasodium pentetate, phytic acid, potassium citrate, sodium citrate, potassium gluconate and sodium gluconate.

38 Claims, No Drawings

SKIN CARE PRODUCTS CONTAINING MULTIPLE ENHANCERS

CROSS REFERENCE TO RELATED APPLICATION

This patent application claims the benefit of U.S. Provisional Application No. 60/976,792, filed Oct. 1, 2007, the disclosures of which are incorporated by reference.

FIELD OF THE INVENTION

The present invention relates to skin care products containing two or more enhancers which increase the beneficial effects of skin care ingredients in the products resulting in enhanced skin care properties.

BACKGROUND INFORMATION

Skin care products have been widely used by consumers and professionals alike in achieving healthy and attractive skin. The present invention aims at improving the effects of skin care agents administered topically by providing skin care products containing the appropriate skin care agent and two or more enhancers.

SUMMARY OF THE INVENTION

The present invention provides a skin care product comprising:

(I) at least two enhancers selected from the group consisting of cyclodextrin, pentasodium pentetate, phytic acid, potassium citrate, sodium citrate, potassium gluconate and sodium gluconate;

(II) at least one optional enhancer selected from the group consisting of ethylene diaminetetraacetic acid (EDTA), EDTA disodium salt, EDTA trisodium salt and EDTA tetrasodium salt; and (III) at least one skin care ingredient selected from:
  (a) alpha-arbutin, hesperidin methyl chalcone, *Glycyrrhiza glabra* (licorice) root extract, *Glycine soja* (soybean) oil, quercetin caprylate, and a mixture of linoleic acid and at least one water soluble ester of ascorbic acid, e.g., sodium ascorbyl phosphate, potassium ascorbyl phosphate, magnesium ascorbyl phosphate and calcium ascorbyl phosphate;
  (b) substances that can increase collagen levels selected from dimethyl sulfone, silymarin and grape (*Vitis vinifera*) seed extract;
  (c) substances that can reduce photoaging grey deposits/brown spots on the skin or reduce hyper-pigmentation, wherein examples of the substances are diacetyl boldine, arbutin, arctostaphylos (*Uva ursi* leaf extract), Tego cosmo and sulfur (e.g., sulfur at about 1 weight % to about 6.5 weight %, preferably, sulfur at about 3.25 weight %);
  (d) enhancers of skin luster, wherein an example of the enhancers is Kombuchka extract (*Saccharomyces/Xylinum* black tea ferment);
  (e) substances that can reduce skin inflammation, wherein the substances are selected from inhiphase (*Pueraria lobata* root extract), quercetin caprylate, bisabolol and silymarin (*Silybum marianum* fruit extract);
  (f) substances that can soothe the skin or reduce skin redness, wherein the substances are selected from licorice (*Glycyrrhiza glabra*) root extract, bisabolol, quercetin caprylate, dipotassium glycyrrhizinate and gatuline (*Ranunculus ficaria* extract);
  (g) skin conditioners selected from aminobutyric acid, bisabolol, *Centella asiatica* extract, *Solanum lycopersicum* (tomato) fruit/leaf/stem extract, jojoba *Simmondsia chinensis* (jojoba) seed oil, *Epilobium angustifolium* flower/leaf/stem extract, tribehenin, chrysin, N-hydroxysuccinimide, phytonadione, oxido reductase and dipeptide-2;
  (h) plant-derived skin care agents or botanical skin care agents selected from *Daucus carota sativa* (carrot) root or its extract, *Arnica montana* flower extract, hydrolyzed rice bran protein, *Ricinus communis* (castor) seed oil, *Butyrospermum parkii* (shea butter), *Theobroma cacao* (cocoa) seed butter, *Solanum lycopersicum* (tomato) fruit/leaf/stem extract, *Vaccinium angustifolium* (blueberry) fruit extract, *Aloe barbadensis* leaf extract, *Punica granatum* (pomegranate) extract, *Salix alba* (willow) bark extract, *Citrus aurantium dulcis* (orange) fruit extract, *Citrus medica limonum* (lemon) fruit extract, *Hamamelis virginiana* (witch hazel) leaf extract, *Glycine soja* (soybean) germ extract, *Pyrus malus* (apple) fruit extract, *Vitis vinifera* (grape) seed extract, *Carthamus tinctorius* (safflower) seed oil, *Oryza sativa* (rice) bran wax, *Vaccinium macrocarpon* (cranberry) seed, *Vaccinium angustifolium* (blueberry) seed, *Origanum majorana* leaf oil, *Citrus aurantium amara* (bitter orange) peel oil, *Anthemis nobilis* flower oil, *Oryza sativa* (rice) bran oil, *Macadamia ternifolia* seed oil, *Laminaria digitata* extract, *Punica granatum* seed extract, *Carica papaya* (papaya) fruit extract, colloidal oatmeal, *Butyrospermum parkii* (shea butter) oil, *Citrus grandis* (grapefruit) peel oil, *Citrus aurantium dulcis* (orange) oil, *Citrus nobilis* (mandarin orange) oil, *Illicium verum* (anise) fruit/seed oil, *Vaccinium macrocarpon* (cranberry) fruit juice, jojoba esters, *Avena sativa* (oat) kernel protein, *Laminaria digitata*, *Citrus aurantium bergamia* (bergamot) fruit oil, *Eugenia caryophyllus* (clove) bud oil, *Coriandrum sativum* (coriander) oil, *Zingiber officinale* (ginger) root oil, *Citrus medica limonum* (lemon) peel oil, *Citrus aurantifolia* (lime) oil, *Litsea cubeba* fruit oil, *Myristica fragrans* (nutmeg) kernel oil, *Citrus aurantium dulcis* (orange) oil, *Lonicera caprifolium* (honeysuckle) flower extract, *Lonicera japonica* (honeysuckle) flower extract, *Rosmarinus officinalis* (rosemary) leaf oil, *Citrus aurantium dulcis* (orange) peel, *Melaleuca alternifolia* (tea tree) oil, *Fucus vesiculosus* (seaweed) extract, *Carica papaya* (papaya) extract, *Hamamelis virginiana* (witch hazel) water, *Cananga odorata* flower oil, *Coffee arabica* (coffee) seed extract, *Saccharomyces/Xylinum*/black tea ferment, *Glyzyrrhiza glabra* (licorice) root extract, *Citrus nobilis* (mandarin orange) fruit extract, *Citrullus vulgaris* (watermelon) fruit extract, caffeine, *Euterpe oleracea* (Acai) fruit extract and *Silybum marianum* fruit extract; and
  (i) miscellaneous skin care agents selected from pearl powder, hexapeptide-10, hydrogenated castor oil, beeswax (*Cera alba*), allantoin, zinc oxide, isononyl isononanoate, isohexadecane, benzoic acid, bentonite, 1-methylhydantoin-2-imide, acrylates/carbamate copolymer, arbutin, lactic acid, mannitol, octoxynol-9, zinc PCA (zinc salt of 1-pyrrolidone carboxylic acid), copper PCA (copper salt of 1-pyrrolidone carboxylic acid), sea salt, cocamidopropyl betaine, citric acid, malic acid, superoxide dismutase, jojoba esters, xanthan gum, caffeine, ectoin and ethylene brassylate.

The at least one skin care ingredient in the skin care product of the present invention can be present, for example, at about 0.01% (w/w) to about 60% (w/w), preferably at about 0.05% (w/w) to about 40% (w/w), more preferably at about 0.1% (w/w) to about 20% (w/w) and even more preferably at about 0.5% (w/w) to about 10% (w/w) and most preferably at about 1% (w/w) to about 5% (w/w).

The skin care product of the present invention can further comprise at least one cosmetically or physiologically acceptable liquid vehicle or carrier, wherein preferably the at least one cosmetically or physiologically acceptable liquid vehicle or carrier is purified water.

The skin care product of the present invention can further comprise at least one emollient/humectant/moisturizer.

The skin care product of the present invention can further comprise at least one active skin care agent other than the skin care ingredients mentioned above. Examples of the at least one active skin care agent include essential oils, antioxidants, free-radical scavengers, reducing agents, collagen stimulating agents, collagen promoters, soluble collagens, self tanners, anti-acne agents, anti-microbial agents, vitamins, skin protecting agents, skin bleaching agents, skin soothing agents, skin conditioners, skin healing agents, anti-redness agents, anti-swelling agents, depuffing agents, substances that can plump the skin and substances that can firm or tone the skin.

The skin care product of the present invention can also comprise at least one skin conditioning agent other than the skin conditioners listed above.

The skin care product of the invention can be applied as a liquid such as a cream or lotion, or as a paste.

The present invention also provides a process of preparing the skin care product of the invention, comprising mixing the components of the specific skin care product described above to form the skin care product.

In one of the embodiments, the present invention provides a method of caring for the skin, comprising rubbing or applying the skin care product of the invention to the skin of a subject, with optional messaging of the one skin care product on and/or into the skin.

In one of the embodiments, the present invention provides a method of caring for the skin, comprising spraying a mist of the skin care product of the invention to the skin of a subject, with optional messaging of the at least one skin care product on and/or into the skin.

In any of the above methods of caring for the skin, the skin care product of the present invention can be applied or sprayed one to six times in a day, or daily at a frequency of one to four times a day.

After and/or before any of the above skin caring methods, one or more additional skin care agents can be optionally applied to the area of the skin. The one or more additional skin care agents optionally applied before and/or after the treatment method can be, but is not limited to, a moisturizer, a skin peel product such as an acid/alkaline skin peel product disclosed in U.S. Pat. No. 7,189,406 issued from U.S. patent application Ser. No. 09/338,729 filed on Jun. 23, 1999 (the disclosure of which application is hereby incorporated by reference), antioxidants, collagen stimulating ingredients, collagen promoters, soluble collagens and/or self tanners.

DETAILED DESCRIPTION OF THE INVENTION

As used herein, the term "enhancer" refers to a substance that can enhance the beneficial effect of at least one skin care ingredient co-administered or co-applied with the substance.

In the present application, the term "subject" means a mammal, preferably a human. The subject can be a human consumer or patient. More preferably, the subject is a human consumer.

The term "physiologically acceptable" modifying a substance means that the substance would cause no significant adverse health effect when administered to the subject. Preferably, a "physiologically acceptable" substance would cause little or no allergic response.

As used herein, the term "cosmetically acceptable" modifying a substance means that the substance is of sufficiently high purity and suitable for use in contact with human skin without undue toxicity, incompatibility and instability. A "cosmetically acceptable" substance, preferably, causes little or no allergic response.

Each of the skin care products of the present invention comprises at least two enhancers selected from the group consisting of cyclodextrin, pentasodium pentetate, phytic acid, potassium citrate, sodium citrate, potassium gluconate and sodium gluconate, with the optional inclusion of at least one optional enhancer selected from the group consisting of ethylene diaminetetraacetic acid (EDTA), EDTA disodium salt, EDTA trisodium salt and EDTA tetrasodium salt. For instance, the skin care product of the present invention comprises at least two enhancers selected from the group consisting of cyclodextrin, pentasodium pentetate, phytic acid, potassium citrate and potassium gluconate, with the optional inclusion of at least one of EDTA, EDTA disodium salt, EDTA trisodium salt and EDTA tetrasodium salt. Preferably, when the skin care product includes citrate as among the at least two enhancers, either potassium citrate or sodium citrate, but not both, is used. Similarly, when the skin care product includes gluconate as among the at least two enhancers, either potassium gluconate or sodium gluconate, but not both, is used. In each of the skin care products of the present invention, each of the enhancers can be present at a level of at least about 0.01%, preferably at least about 0.02%, more preferably at least about 0.1%, even more preferably at least about 0.2% by weight of the skin care product. For instance, each of the enhancers in each of the skin care products of the present invention can be present at a level ranging from about 0.01% to about 1%, preferably ranging from about 0.02% to about 0.5%, more preferably ranging from about 0.1% to about 0.25%, e.g., at a level of 0.01%, 0.02%, 0.05%, 0.1%, 0.167%, 0.2% or 0.3%, by weight of the skin care product. In each of the skin care products of the present invention, the total levels of all the enhancers combined can range from about 0.05% to about 10%, more preferably from about 0.1% to about 5%, even more preferably from about 0.2% to about 2%, e.g., at about 0.2%, about 0.3%, about 0.4%, about 0.7%, about 1%, about 1.1% or about 1.2%, by weight of the skin care product.

An embodiment of the skin care products of the present invention comprises at least three enhancers, e.g., three or four enhancers, selected from the group consisting of cyclodextrin, pentasodium pentetate, phytic acid, potassium citrate, sodium citrate, potassium gluconate and sodium gluconate, wherein preferably potassium citrate and sodium citrate are not present together, and potassium gluconate and sodium gluconate are not present together. Optionally, the skin care product further comprises at least one additional enhancer, e.g., one, two or three, selected from the group consisting of ethylene diaminetetraacetic acid (EDTA), EDTA disodium salt, EDTA trisodium salt and EDTA tetrasodium salt.

Another embodiments of the skin care products of the present invention comprises at least four enhancers, e.g., five or six enhancers, selected from the group consisting of cyclodextrin, pentasodium pentetate, phytic acid, potassium citrate, sodium citrate, potassium gluconate and sodium gluconate, wherein preferably potassium citrate and sodium citrate are not present together, and potassium gluconate and sodium gluconate are not present together. Optionally, the skin care product further comprises at least one additional enhancer, e.g., one, two or three, selected from the group consisting of ethylene diaminetetraacetic acid (EDTA), EDTA disodium salt, EDTA trisodium salt and EDTA tetrasodium salt.

Suitable emollient/humectant/moisturizer that can be used in the skin care products of the invention include the emullients and moisturizing agents disclosed below. Examples of emullients that can be used in the skin moisturizing products of the invention are glycerin, cetyl alcohol, cetearyl isononanoate, cetearyl octanoate, decyl oleate, isooctyl stearate, coco caprylate/caprate, ethylhexyl hydroxystearate, ethylhexyl isononanoate, isoproyl palmitate, isopropyl isostearate, isopropyl myristate, oleyl oleate, hexyl laurate, paraffinum liquidum, PEG-75 lanolin, PEG-7 glyceryl cocoate, petrolatum, ozokerite, cyclomethicone, dimethicone, dimethicone copolyol, dicaprylyl ether, *butyrospermum parkii, buxus chinensis*, canola, *carnauba cera, copernicia cerifera, oenothera biennis, elaeis guineensis, prunus dulcis*, squalane, *zea mays, glycine soja, helianthus annuus*, lanolin, hydrogenated castor oil, hydrogenated coconut oil, avocodo oil, hydrogenated polyisobutene, sucrose cocoate, stearoxy dimethicone, lanolin alcohol, isohexadecane. Examples of moisturizing agents that can be used are butylene glycol, cetyl alcohol, dimethicone, dimyristyl tartrate, glucose, glycereth-26, glycerin, glyceryl stearate, hydrolyzed milk protein, lactic acid, lactose and other sugars, laureth-8, lecithin, octoxyglycerin, PEG-12, PEG-135, PEG-150, PEG-20, PEG-8, pentylene glycol, hexylene glycol, phytantriol, polyquaternium-39, PPG-20 methyl glucose ether, propylene glycol, sodium hyaluronate, sodium lactate, sodium PCA (sodium salt of 1-pyrrolidone carboxylic acid), sorbitol, succinoglycan, synthetic beeswax, tri-C14 15 alkyl citrate, starch.

As used herein, the term "anti-acne agent" means a substance that have a beneficial effect in treating or preventing acne. Suitable anti-acne agents can be drying agents, keratolytic agents, epidermolytic agents, antimicrobial agents and retinoids. Examples of anti-acne agents include sulfur, resorcinol, glycolic acid, lactic acid, pyruvic acid, salicylic acid, retinoic acid, derivatives of retinoic acid, and antimicrobial agents, e.g., farnesol, benzoyl peroxide, erythromycin, triclosan, azelaic acid, clindamycin, chlorhexidine, neomycin, miconazole, clotrimazole and tetracycline. Suitable anti-acne agents include salicylic acid; 5-octanoyl salicylic acid; resorcinol; retinoids such as retinoic acid and its derivatives; sulfur-containing D and L amino acids other than cysteine; lipoic acid; antibiotics and antimicrobials such as benzoyl peroxide, octopirox, tetracycline, 2,4,4'-trichloro-2'-hydroxydiphenyl ether, 3,4,4'-trichlorobanilide, azelaic acid, phenoxyethanol, phenoxypropanol, phenoxisopropanol, ethyl acetate, clindamycin and melclocycline; flavonoids; and bile salts such as scymnol sulfate, deoxycholate and cholate.

The term "skin care agent" refers to an agent that has one or more beneficial effects on the care and/or hygiene of the skin. The skin care agent can be selected from the group consisting of antioxidants, free-radical scavengers, antimicrobial agents, anti-acne agents, reducing agents, vitamins, skin protecting agents, skin bleaching agents, skin conditioning agents, skin soothing agents, skin healing agents, collagen promoters, exfoliators, self tanners, chelators, hair removers, anti-erythema agents, anti-redness agents, anti-rosacea agents, depuffing agents, anti-edema agents, anti-swelling agents, hyaluronic acid, green tea extract, *P. emblica* (Amla), *arnica*, chamomile extract and cucumber extract. The skin care agent is, preferably, selected from the group consisting of skin protecting agents, skin conditioning agents, antioxidants, anti-acne agents, collagen promoters, soluble collagen, self tanner and mixtures thereof. More preferably, the skin care agent is selected from antiwrinkle agents, anti-skin-atrophy agents, antioxidants and anti-acne agents.

The skin protecting agents are agents that protect the skin against chemical irritants and/or physical irritants, e.g., UV light, including sunscreens, anti-acne additives, anti-wrinkle and anti-skin atrophy agents.

Suitable UV blocking agents include 2-ethylhexyl p-methoxycinnamate, 2-ethylhexyl N,N-dimethyl-p-aminobenzoate, p-aminobenzoic acid, 2-phenylbenzimidazole-5-sulfonic acid, octocrylene, oxybenzone, homomethyl salicylate, octyl salicylate, 4,4'-methoxy-t-butyldibenzoylmethane, 4-isopropy dibenzoylmethane, 3-benzylidene camphor, 3-(4-methylbenzylidene)camphor, anthanilates, ultrafine titanium dioxide, zinc oxide, iron oxide, silica, 4-N,N-(2-ethylhexyl) methylaminobenzoic acid ester of 2,4-dihydroxybenzophenone, 4-N,N-(2-ethylhexyl)-methylaminobenzoic acid ester with 4-hydroxydibenzoylmethane, 4-N,N-(2-ethylhexyl)-methylaminobenzoic acid ester of 2-hydroxy-4-(2-hydroxyethoxy)benzophenone and 4-N,N(2-ethylhexyl)-methylaminobenzoic acid ester of 4-(2-hydroxyethoxy) dibenzoylmethane.

Examples of anti-wrinkle and anti-skin atrophy agents are retinoic acid and its derivatives, retinol, retinyl esters, salicylic acid and its derivatives, sulfur-containing D and L amino acids except cysteine, alpha-hydroxy acids (e.g., glycolic acid and lactic acid), phytic acid, lipoic acid and lysophosphatidic acid.

The skin care products of the invention, preferably, further comprise at least one emollient/humectant/moisturizer (e.g., butylene glycol) and/or at least one additional active ingredient, at least one cosmetically acceptable aesthetic component and/or at least one cosmetically acceptable excipient.

The at least one cosmetically acceptable vehicle or carrier is, preferably, a liquid, which is preferably water or a cosmetically acceptable aqueous buffer having a pH of about 7.0 to about 7.4, and, more preferably, the water or aqueous buffer is purified and/or sterile.

The at least one cosmetically acceptable excipient is, preferably, selected from the group consisting of surfactant/emulsifying agents, absorbents, antifoaming agents, binders, biological additives, chelating agents, denaturants, preservatives, solubilizing agents, solvents and thickening agents.

The at least one additional active ingredient is, preferably, selected from the group consisting of antioxidants, free-radical scavengers, antimicrobial agents, topical analgesics, steroidal anti-inflammatory drugs, anti-acne agents, reducing agents, vitamins, skin protecting agents, skin bleaching agents, skin conditioning agents, skin soothing agents, skin healing agents, collagen promoters, exfoliators, self tanners, chelators, hair removers, anti-erythema agents, anti-redness agents, anti-rosacea agents, depuffing agents, anti-edema agents, anti-swelling agents, green tea extract, *P. emblica* (Amla), *arnica*, chamomile extract and cucumber extract. The at least one active ingredient is, preferably, at least one antioxidant, anti-acne agent, collagen promoter, soluble collagen, self tanner or mixtures thereof. More preferably, the at least one additional active ingredient is at least one antioxidant or anti-acne agent.

Suitable collagen promoters are peptides.

Suitable surfactant/emulsifying agents include ceteareths, ceteths, laneths, laureths, isoseareths, steareths, cetyl alcohol, deceths, dodoxynols, glyceryl palmitate, glyceryl stearate, laneths, myreths, nonoxynols, octoxynols, oleths, PEG-castor oil, poloxamers (e.g., poloxamer 407), poloxamines, polysorbates, sodium laurate, ammonium laureth sulfate, sodium laureth sulfate, sodium lauroyl sarcosinate, sodium lauroyl taurate, sodium lauryl sulfate, sodium methyl cocoyl taurate, sodium methyl oleoyl taurate, sodium nonoxynol sulfate, sodium cetyl sulfate, sodium cetearyl sulfate, sodium cocoate, sodium cocoyl isethionate and sodium cocoyl sarcosinate. Other suitable surfactant/emulsifying agents would be known to one of skill in the art and are listed in the *CTFA International Cosmetic Ingredient Dictionary and Handbook*, Vol. 2, 7th Edition (1997). Preferred surfactants include octoxynol-9 and polysorbate-20.

Examples of suitable preservatives include imidazolidinyl urea, diazolidinyl urea, phenoxyethanol, methylparaben, ethylparaben and propylparaben.

Examples of thickening agents include isopropyl myristate, isopropyl palmitate, isodecyl neopentanoate, squalene, mineral oil, $C_{12}$-$C_{15}$ benzoate and hydrogenated polyisobutene.

Examples of antioxidants and/or free-radical scavengers include ascorbic acid, salts of ascorbic acid such as ascorbyl palmitate and sodium ascorbate, ascorbyl glucosamine, vitamin E (i.e., tocopherols such as α-tocopherol), derivatives of vitamin E (e.g., tocopheryl acetate), retinoids such as retinoic acid, retinol, trans-retinol, cis-retinol, mixtures of trans-retinol and cis-retinol, 3-dehydroretinol and derivatives of vitamin A (e.g., retinyl acetate, retinal and retinyl palmitate, also known as tetinyl palmitate), lipoic acid, sodium citrate, sodium sulfite, lycopene, anthocyanids, bioflavinoids (e.g., hesperitin, naringen, rutin and quercetin), superoxide dismutase, glutathione peroxidase, butylated hydroxytoluene (BHT), butylated hydroxyanisole (BHA), indole-3-carbinol, pycnogenol, melatonin, sulforaphane, pregnenolone, lipoic acid and 4-hydroxy-5-methyl-3 [2H]-furanone.

The antimicrobial agents can be antibacterial agents and/or antifungal agents. Examples of the antimicrobial agents include farnesol, benzoyl peroxide, erythromycin, tetracycline, triclosan, azelaic acid, clindamycin, chlorhexidine, neomycin, miconazole and clotrimazole.

The skin conditioning agents can be emollients, humectants and moisturizers, which include urea; guanidine; aloe vera; glycolic acid and glycolate salts such as ammonium and quaternary alkyl ammonium; lactic acid and lactate salts such as sodium lactate, ammonium lactate and quaternary alkyl ammonium lactate; polyhydroxy alcohols such as sorbitol, glycerol, hexanetriol, propylene glycol, butylene glycol, hexylene glycol, polyethylene glycol; carbohydrates such as alkoxylated glucose; starches; starch derivatives; glycerin; pyrrolidone carboxylic acid (PCA); lactamide monoethanolamine; acetamide monoethanolamine; volatile silicone oils; nonvolatile silicone oils; and mixtures thereof. Suitable silicone oils can be polydialkylsiloxanes, polydiarylsiloxanes, polyalkarylsiloxanes and cyclomethicones having 3 to 9 silicon atoms.

Skin soothing agents include bisabolol.

Suitable skin bleaching agents include, for example, hydroquinone, kojic acid and sodium metabisulfite.

The at least one aesthetic agent can be at least one of fragrances, pigments, colorants, essential oils, skin sensates and astringents. Examples of the suitable essential oils are olive oil, rose oil, palm oil, lavender oil, almond oil, *Oenothera biennis* (evening primrose) oil, clove oil, eucalyptus oil, peppermint oil and spearmint oil. Suitable aesthetic agents include clove oil, menthol, camphor, eucalyptus oil, eugenol, methyl lactate, bisabolol, witch hazel distillate (preferred) and green tea extract (preferred).

The at least one anti-oxidant preferably is selected from ascorbic acid, ascorbyl palmitate, ascorbyl glucosamine, tocopheryl acetate, retinyl palmitate, superoxide dismutase, or mixtures thereof. The at least one skin conditioning agent preferably is selected from cyclomethicone and/or dimethiconol. The at least one reducing agent preferably is ubiquinone. The at least one additional active agent can be *Camellia sinensis* leaf extract and/or white tea extract or juice, preferably *Camellia sinensis* leaf extract. The at least one cosmetically acceptable vehicle or carrier can be purified or sterile water, preferably purified water. The at least one cosmetically acceptable excipient can be phospholipids.

The present invention also provides a skin care product having the components listed in the following table.

| COMPONENTS | % (w/w) |
| --- | --- |
| CYCLOPENTASILOXANE | 5 to 80 |
| CYCLOMETHICONE | 1 to 60 |
| ASCORBIC ACID | 1 to 20 |
| DIMETHICONE CROSSPOLYMER | 1 to 20 |
| PEG/PPG-18/18 DIMETHICONE | 0 to 5 |
| SQUALANE | 0 to 5 |
| PURIFIED WATER (AQUA PURIFICATA) | 0 to 5 |
| ACRYLATES/CARBAMATE COPOLYMER | 0 to 5 |
| ASCORBYL PALMITATE | 0 to 5 |
| BUTYLENE GLYCOL | 0 to 5 |
| LINOLEIC ACID | 0 to 5 |
| PALMITOYL OLIGOPEPTIDE | 0 to 5 |
| PANTHENOL | 0 to 5 |
| *PUERARIA LOBATA* ROOT EXTRACT | 0 to 5 |
| QUERCETIN CAPRYLATE | 0 to 5 |
| SALICYLIC ACID | 0 to 5 |
| *SALIX NIGRA* (WILLOW) BARK EXTRACT | 0 to 5 |
| SODIUM ASCORBYL PHOSPHATE | 0 to 5 |
| SODIUM CHONDROITIN SULFATE | 0 to 5 |
| SODIUM HYALURONATE | 0 to 5 |
| TOCOPHERYL ACETATE | 0 to 5 |
| LACTIC ACID | 0 to 5 |
| PENTASODIUM PENTETATE | 0 to 5, e.g., 0.005 to 2 |
| PHENOXYETHANOL | 0 to 5, e.g., 0.005 to 2 |
| PHYTIC ACID | 0 to 5, e.g., 0.005 to 2 |
| POTASSIUM CITRATE | 0 to 5, e.g., 0.005 to 2 |
| POTASSIUM GLUCONATE | 0 to 5, e.g., 0.005 to 2 |
| TETRASODIUM EDTA | 0 to 5, e.g., 0.005 to 2 |
| | 100% |

The present invention also provides a skin care product having the components listed in the following table.

| COMPONENTS | % (w/w) |
| --- | --- |
| CYCLOPENTASILOXANE | 48.600000 |
| CYCLOMETHICONE | 28.370000 |
| ASCORBIC ACID | 10.000000 |
| DIMETHICONE CROSSPOLYMER | 9.400000 |
| PEG/PPG-18/18 DIMETHICONE | 1.000000 |
| SQUALANE | 1.000000 |
| PURIFIED WATER (AQUA PURIFICATA) | 0.200000 |
| ACRYLATES/CARBAMATE COPOLYMER | 0.100000 |
| ASCORBYL PALMITATE | 0.100000 |
| BUTYLENE GLYCOL | 0.100000 |
| LINOLEIC ACID | 0.100000 |
| PALMITOYL OLIGOPEPTIDE | 0.100000 |
| PANTHENOL | 0.100000 |
| *PUERARIA LOBATA* ROOT EXTRACT | 0.100000 |
| QUERCETIN CAPRYLATE | 0.100000 |
| SALICYLIC ACID | 0.100000 |

-continued

| COMPONENTS | % (w/w) |
|---|---|
| *SALIX NIGRA* (WILLOW) BARK EXTRACT | 0.100000 |
| SODIUM ASCORBYL PHOSPHATE | 0.100000 |
| SODIUM CHONDROITIN SULFATE | 0.100000 |
| SODIUM HYALURONATE | 0.100000 |
| TOCOPHERYL ACETATE | 0.100000 |
| LACTIC ACID | 0.010000 |
| PENTASODIUM PENTETATE | 0.010000 |
| PHENOXYETHANOL | 0.010000 |
| PHYTIC ACID | 0.010000 |
| POTASSIUM CITRATE | 0.010000 |
| POTASSIUM GLUCONATE | 0.010000 |
| TETRASODIUM EDTA | 0.010000 |
|  | 100% |

The present invention also provides a skin care product having the components listed in the following table.

| COMPONENTS | % (w/w) |
|---|---|
| WATER (AQUA) | 5 to 90 |
| *ALOE BARBADENSIS* LEAF JUICE | 0 to 10 |
| CETEARYL ALCOHOL | 0 to 10 |
| CYCLOPENTASILOXANE | 0 to 10 |
| GLYCERIN | 0 to 10 |
| C12-15 ALKYL BENZOATE | 0 to 10 |
| SQUALANE | 0 to 10 |
| *CAMELLIA SINENSIS* LEAF EXTRACT | 0 to 5 |
| DIMETHICONE | 0 to 5 |
| PEG/PPG-18/18 DIMETHICONE | 0 to 5 |
| PHENOXYETHANOL | 0 to 5 |
| SODIUM PCA | 0 to 5 |
| CAPRYLYL GLYCOL | 0 to 5 |
| PPG-2 MYRISTYL ETHER PROPIONATE | 0 to 5 |
| TRIETHANOLAMINE | 0 to 5 |
| CARBOMER | 0 to 5 |
| *CUCUMIS SATIVUS* (CUCUMBER) FRUIT EXTRACT | 0 to 5 |
| METHYLPARABEN | 0 to 5 |
| SODIUM POLYACRYLATE | 0 to 5 |
| POLYSORBATE 60 | 0 to 5 |
| TRIDECETH-6 | 0 to 5 |
| ASCORBYL PALMITATE | 0 to 5 |
| BUTYLENE GLYCOL | 0 to 5 |
| CERAMIDE 2 | 0 to 5 |
| COPPER PCA | 0 to 5 |
| DIMETHYL SULFONE | 0 to 5 |
| DISODIUM EDTA | 0 to 5 |
| *EMBLICA OFFICINALIS* FRUIT EXTRACT | 0 to 5 |
| LACTIC ACID | 0 to 5 |
| LINOLEIC ACID | 0 to 5 |
| PANTHENOL | 0 to 5 |
| PEG-10 RAPESEED STEROL | 0 to 5 |
| PHOSPHOLIPIDS | 0 to 5 |
| POLYSORBATE 20 | 0 to 5 |
| PROPYLPARABEN | 0 to 5 |
| RETINOL | 0 to 5 |
| RETINYL PALMITATE | 0 to 5 |
| *SILYBUM MARIANUM* FRUIT EXTRACT | 0 to 5 |
| SODIUM HYALURONATE | 0 to 5 |
| *SOLANUM LYCOPERSICUM* (TOMATO) FRUIT/LEAF/STEM EXTRACT | 0 to 5 |
| SOY ISOFLAVONES | 0 to 5 |
| TETRASODIUM EDTA | 0 to 5 |
| TOCOPHERYL ACETATE | 0 to 5 |
| TRIBEHENIN | 0 to 5 |
| UBIQUINONE | 0 to 5 |
| *VITIS VINIFERA* (GRAPE) SEED EXTRACT | 0 to 5 |
| ZINC PCA | 0 to 5 |
| ACRYLATES/CARBAMATE COPOLYMER | 0 to 5 |
| ASCORBIC ACID | 0 to 5 |
| SORBIC ACID | 0 to 5 |
| CYCLODEXTRIN | 0 to 5 |
| PENTASODIUM PENTETATE | 0 to 5 |
| PHYTIC ACID | 0 to 5 |
| POTASSIUM CITRATE | 0 to 5 |
| POTASSIUM GLUCONATE | 0 to 5 |
| PALMITOYL OLIGOPEPTIDE | 0 to 5 |
| PALMITOYL PENTAPEPTIDE-3 | 0 to 5 |
|  | 100% |

The present invention also provides a skin care product having the components listed in the following table.

| COMPONENTS | % (w/w) |
|---|---|
| WATER (AQUA) | 70.330000 |
| *ALOE BARBADENSIS* LEAF JUICE | 4.000000 |
| CETEARYL ALCOHOL | 4.000000 |
| CYCLOPENTASILOXANE | 4.000000 |
| GLYCERIN | 3.000000 |
| C12-15 ALKYL BENZOATE | 2.800000 |
| SQUALANE | 2.800000 |
| *CAMELLIA SINENSIS* LEAF EXTRACT | 1.000000 |
| DIMETHICONE | 1.000000 |
| PEG/PPG-18/18 DIMETHICONE | 1.000000 |
| PHENOXYETHANOL | 0.520000 |
| SODIUM PCA | 0.500000 |
| CAPRYLYL GLYCOL | 0.430000 |
| PPG-2 MYRISTYL ETHER PROPIONATE | 0.400000 |
| TRIETHANOLAMINE | 0.250000 |
| CARBOMER | 0.220000 |
| *CUCUMIS SATIVUS* (CUCUMBER) FRUIT EXTRACT | 0.200000 |
| METHYLPARABEN | 0.200000 |
| SODIUM POLYACRYLATE | 0.200000 |
| POLYSORBATE 60 | 0.150000 |
| TRIDECETH-6 | 0.150000 |
| ASCORBYL PALMITATE | 0.100000 |
| BUTYLENE GLYCOL | 0.100000 |
| CERAMIDE 2 | 0.100000 |
| COPPER PCA | 0.100000 |
| DIMETHYL SULFONE | 0.100000 |
| DISODIUM EDTA | 0.100000 |
| *EMBLICA OFFICINALIS* FRUIT EXTRACT | 0.100000 |
| LACTIC ACID | 0.100000 |
| LINOLEIC ACID | 0.100000 |
| PANTHENOL | 0.100000 |
| PEG-10 RAPESEED STEROL | 0.100000 |
| PHOSPHOLIPIDS | 0.100000 |
| POLYSORBATE 20 | 0.100000 |
| PROPYLPARABEN | 0.100000 |
| RETINOL | 0.100000 |
| RETINYL PALMITATE | 0.100000 |
| *SILYBUM MARIANUM* FRUIT EXTRACT | 0.100000 |
| SODIUM HYALURONATE | 0.100000 |
| *SOLANUM LYCOPERSICUM* (TOMATO) FRUIT/LEAF/STEM EXTRACT | 0.100000 |
| SOY ISOFLAVONES | 0.100000 |
| TETRASODIUM EDTA | 0.100000 |
| TOCOPHERYL ACETATE | 0.100000 |
| TRIBEHENIN | 0.100000 |
| UBIQUINONE | 0.100000 |
| *VITIS VINIFERA* (GRAPE) SEED EXTRACT | 0.100000 |
| ZINC PCA | 0.100000 |
| ACRYLATES/CARBAMATE COPOLYMER | 0.050000 |
| ASCORBIC ACID | 0.050000 |
| SORBIC ACID | 0.050000 |
| CYCLODEXTRIN | 0.020000 |
| PENTASODIUM PENTETATE | 0.020000 |
| PHYTIC ACID | 0.020000 |
| POTASSIUM CITRATE | 0.020000 |
| POTASSIUM GLUCONATE | 0.020000 |
| PALMITOYL OLIGOPEPTIDE | 0.000002 |
| PALMITOYL PENTAPEPTIDE-3 | 0.000002 |
|  | 100% |

The present invention also provides a skin care product having the components listed in the following table.

| COMPONENTS | % (w/w) |
| --- | --- |
| WATER (AQUA) | 1 to 90 |
| CAPRYLIC/CAPRIC TRIGLYCERIDE | 0 to 20 |
| CYCLOMETHICONE | 0 to 20 |
| DIMETHICONE | 0 to 20 |
| ETHYL MACADAMIATE | 0 to 20 |
| BUTYLENE GLYCOL | 0 to 10 |
| GLYCERIN | 0 to 10 |
| SODIUM PCA | 0 to 10 |
| GLYCERYL STEARATE | 0 to 10 |
| CETEARYL ETHYLHEXANOATE | 0 to 10 |
| HEXAPETIDE-10 | 0 to 10 |
| DEA-CETYL PHOSPHATE | 0 to 10 |
| POLYSORBATE 20 | 0 to 10 |
| SQUALANE | 0 to 10 |
| ISOSTEARYL LINOLEATE | 0 to 5 |
| PETROLATUM | 0 to 5 |
| STEARYL ALCOHOL | 0 to 5 |
| PALMITIC ACID | 0 to 5 |
| HECTORITE | 0 to 5 |
| MAGNESIUM ALUMINUM SILICATE | 0 to 5 |
| *OENOTHERA BIENNIS* (EVENING PRIMROSE) OIL | 0 to 5 |
| PHENOXYETHANOL | 0 to 5 |
| PEG-100 STEARATE | 0 to 5 |
| SORBIC ACID | 0 to 5 |
| CAPRYLYL GLYCOL | 0 to 5 |
| *LAVANDULA ANGUSTIFOLIA* (LAVENDER) OIL | 0 to 5 |
| DISODIUM LAURIMINODIPROPIONATE TOCOPHERYL PHOSPHATES | 0 to 5 |
| PEG-12 DIMETHICONE | 0 to 5 |
| BEHENYL ALCOHOL | 0 to 5 |
| LAURYL ALCOHOL | 0 to 5 |
| PROPYLENE GLYCOL | 0 to 5 |
| *CENTELLA ASIATICA* EXTRACT | 0 to 5 |
| BISABOLOL | 0 to 5 |
| CETYL ALCOHOL | 0 to 5 |
| *EMBLICA OFFICINALIS* FRUIT EXTRACT | 0 to 5 |
| MYRISTYL ALCOHOL | 0 to 5 |
| *PRUNUS AMYGDALUS DULCIS* (SWEET ALMOND) OIL | 0 to 5 |
| TETRASODIUM EDTA | 0 to 5 |
| *OLEA EUROPAEA* (OLIVE) FRUIT OIL | 0 to 5 |
| LECITHIN | 0 to 5 |
| TRIDECETH-6 | 0 to 5 |
| ASCORBIC ACID | 0 to 5 |
| CYCLODEXTRIN | 0 to 5 |
| PENTASODIUM PENTETATE | 0 to 5 |
| PHYTIC ACID | 0 to 5 |
| POLYMETHYL METHACRYLATE | 0 to 5 |
| POLYQUATERNIUM-51 | 0 to 5 |
| POTASSIUM CITRATE | 0 to 5 |
| POTASSIUM GLUCONATE | 0 to 5 |
| SODIUM HYALURONATE | 0 to 5 |
| SODIUM POLYACRYLATE | 0 to 5 |
| UREA | 0 to 5 |
| ASCORBYL PALMITATE | 0 to 5 |
| CARBOMER | 0 to 5 |
| CERAMIDE 2 | 0 to 5 |
| HYDROGENATED POLYDECENE | 0 to 5 |
| PHOSPHOLIPIDS | 0 to 5 |
| RETINYL PALMITATE | 0 to 5 |
| SOY ISOFLAVONES | 0 to 5 |
| TOCOPHERYL ACETATE | 0 to 5 |
| TREHALOSE | 0 to 5 |
| UBIQUINONE | 0 to 5 |
| PALMITOYL TETRAPEPTIDE-3 | 0 to 5 |
| DNA | 0 to 5 |
| | 100% |

The present invention also provides a skin care product having the components listed in the following table.

| COMPONENTS | % (w/w) |
| --- | --- |
| WATER (AQUA) | 41.160000 |
| CAPRYLIC/CAPRIC TRIGLYCERIDE | 8.930000 |
| CYCLOMETHICONE | 7.510000 |
| DIMETHICONE | 7.250000 |
| ETHYL MACADAMIATE | 5.000000 |
| BUTYLENE GLYCOL | 3.500000 |
| GLYCERIN | 3.270000 |
| SODIUM PCA | 3.270000 |
| GLYCERYL STEARATE | 2.000000 |
| CETEARYL ETHYLHEXANOATE | 1.800000 |
| HEXAPETIDE-10 | 1.800000 |
| DEA-CETYL PHOSPHATE | 1.310000 |
| POLYSORBATE 20 | 1.310000 |
| SQUALANE | 1.310000 |
| ISOSTEARYL LINOLEATE | 1.000000 |
| PETROLATUM | 1.000000 |
| STEARYL ALCOHOL | 1.000000 |
| PALMITIC ACID | 0.700000 |
| HECTORITE | 0.650000 |
| MAGNESIUM ALUMINUM SILICATE | 0.650000 |
| *OENOTHERA BIENNIS* (EVENING PRIMROSE) OIL | 0.650000 |
| PHENOXYETHANOL | 0.520000 |
| PEG-100 STEARATE | 0.500000 |
| SORBIC ACID | 0.500000 |
| CAPRYLYL GLYCOL | 0.430000 |
| *LAVANDULA ANGUSTIFOLIA* (LAVENDER) OIL | 0.390000 |
| DISODIUM LAURIMINODIPROPIONATE TOCOPHERYL PHOSPHATES | 0.330000 |
| PEG-12 DIMETHICONE | 0.330000 |
| BEHENYL ALCOHOL | 0.300000 |
| LAURYL ALCOHOL | 0.200000 |
| PROPYLENE GLYCOL | 0.200000 |
| *CENTELLA ASIATICA* EXTRACT | 0.150000 |
| BISABOLOL | 0.100000 |
| CETYL ALCOHOL | 0.100000 |
| *EMBLICA OFFICINALIS* FRUIT EXTRACT | 0.100000 |
| MYRISTYL ALCOHOL | 0.100000 |
| *PRUNUS AMYGDALUS DULCIS* (SWEET ALMOND) OIL | 0.100000 |
| TETRASODIUM EDTA | 0.100000 |
| *OLEA EUROPAEA* (OLIVE) FRUIT OIL | 0.080000 |
| LECITHIN | 0.050000 |
| TRIDECETH-6 | 0.030000 |
| ASCORBIC ACID | 0.020000 |
| CYCLODEXTRIN | 0.020000 |
| PENTASODIUM PENTETATE | 0.020000 |
| PHYTIC ACID | 0.020000 |
| POLYMETHYL METHACRYLATE | 0.020000 |
| POLYQUATERNIUM-51 | 0.020000 |
| POTASSIUM CITRATE | 0.020000 |
| POTASSIUM GLUCONATE | 0.020000 |
| SODIUM HYALURONATE | 0.020000 |
| SODIUM POLYACRYLATE | 0.020000 |
| UREA | 0.020000 |
| ASCORBYL PALMITATE | 0.010000 |
| CARBOMER | 0.010000 |
| CERAMIDE 2 | 0.010000 |
| HYDROGENATED POLYDECENE | 0.010000 |
| PHOSPHOLIPIDS | 0.010000 |
| RETINYL PALMITATE | 0.010000 |
| SOY ISOFLAVONES | 0.010000 |
| TOCOPHERYL ACETATE | 0.010000 |
| TREHALOSE | 0.010000 |
| UBIQUINONE | 0.010000 |
| PALMITOYL TETRAPEPTIDE-3 | 0.000002 |
| DNA | 0.000001 |
| | 100% |

The present invention also provides a skin care product having the components listed in the following table.

| COMPONENTS | % (w/w) |
| --- | --- |
| WATER (AQUA) | 5 to 90 |
| CYCLOMETHICONE | 1 to 20 |
| GLYCERIN | 0 to 10 |
| SODIUM PCA | 0 to 10 |
| CYCLOPENTASILOXANE | 0 to 5 |

| COMPONENTS | % (w/w) |
|---|---|
| DIMETHICONE | 0 to 5 |
| PEG/PPG-18/18 DIMETHICONE | 0 to 5 |
| *OENOTHERA BIENNIS* (EVENING PRIMROSE) OIL | 0 to 5 |
| PHENOXYETHANOL | 0 to 5 |
| BUTYLENE GLYCOL | 0 to 5 |
| CAPRYLYL GLYCOL | 0 to 5 |
| GLYCERYL STEARATE | 0 to 5 |
| CETEARYL ETHYLHEXANOATE | 0 to 5 |
| CAPRYLIC/CAPRIC TRIGLYCERIDE | 0 to 5 |
| SODIUM POLYACRYLATE | 0 to 5 |
| DEA-CETYL PHOSPHATE | 0 to 5 |
| SQUALANE | 0 to 5 |
| BEHENYL ALCOHOL | 0 to 5 |
| CETYL ALCOHOL | 0 to 5 |
| ISOSTEARYL LINOLEATE | 0 to 5 |
| LAURYL ALCOHOL | 0 to 5 |
| LECITHIN | 0 to 5 |
| MYRISTYL ALCOHOL | 0 to 5 |
| PALMITIC ACID | 0 to 5 |
| PETROLATUM | 0 to 5 |
| STEARYL ALCOHOL | 0 to 5 |
| HECTORITE | 0 to 5 |
| HYDROGENATED POLYDECENE | 0 to 5 |
| MAGNESIUM ALUMINUM SILICATE | 0 to 5 |
| *OLEA EUROPAEA* (OLIVE) FRUIT OIL | 0 to 5 |
| PEG-100 STEARATE | 0 to 5 |
| PEG-12 DIMETHICONE | 0 to 5 |
| POLYSORBATE 20 | 0 to 5 |
| PROPYLENE GLYCOL | 0 to 5 |
| STEARETH-20 | 0 to 5 |
| TETRASODIUM EDTA | 0 to 5 |
| TRIDECETH-6 | 0 to 5 |
| *LAVANDULA ANGUSTIFOLIA* (LAVENDER) OIL | 0 to 5 |
| ACRYLATES/CARBAMATE COPOLYMER | 0 to 5 |
| DISODIUM LAURIMINODIPROPIONATE TOCOPHERYL PHOSPHATES | 0 to 5 |
| SORBIC ACID | 0 to 5 |
| SODIUM HYALURONATE | 0 to 5 |
| CYCLODEXTRIN | 0 to 5 |
| PENTASODIUM PENTETATE | 0 to 5 |
| PHYTIC ACID | 0 to 5 |
| POTASSIUM CITRATE | 0 to 5 |
| POTASSIUM GLUCONATE | 0 to 5 |
| RETINOL | 0 to 5 |
| *SOLANUM LYCOPERSICUM* (TOMATO) FRUIT/LEAF/STEM EXTRACT | 0 to 5 |
| ASCORBYL PALMITATE | 0 to 5 |
| CERAMIDE 2 | 0 to 5 |
| COPPER PCA | 0 to 5 |
| *EMBLICA OFFICINALIS* FRUIT EXTRACT | 0 to 5 |
| MICA | 0 to 5 |
| PHOSPHOLIPIDS | 0 to 5 |
| *PRUNUS AMYGDALUS DULCIS* (SWEET ALMOND) OIL | 0 to 5 |
| RETINYL PALMITATE | 0 to 5 |
| SOY ISOFLAVONES | 0 to 5 |
| TITANIUM DIOXIDE (CI 77891) | 0 to 5 |
| TOCOPHERYL ACETATE | 0 to 5 |
| UBIQUINONE | 0 to 5 |
| ZINC PCA | 0 to 5 |
| AMINOBUTYRIC ACID | 0 to 5 |
| PALMITOYL TETRAPEPTIDE-3 | 0 to 5 |
| | 100% |

The present invention also provides a skin care product having the components listed in the following table.

| COMPONENTS | % (w/w) |
|---|---|
| WATER (AQUA) | 79.420000 |
| CYCLOMETHICONE | 5.980000 |
| GLYCERIN | 2.500000 |
| SODIUM PCA | 2.500000 |
| CYCLOPENTASILOXANE | 1.000000 |
| DIMETHICONE | 1.000000 |
| PEG/PPG-18/18 DIMETHICONE | 1.000000 |
| *OENOTHERA BIENNIS* (EVENING PRIMROSE) OIL | 0.600000 |
| PHENOXYETHANOL | 0.580000 |
| BUTYLENE GLYCOL | 0.480000 |
| CAPRYLYL GLYCOL | 0.430000 |
| GLYCERYL STEARATE | 0.350000 |
| CETEARYL ETHYLHEXANOATE | 0.300000 |
| CAPRYLIC/CAPRIC TRIGLYCERIDE | 0.250000 |
| SODIUM POLYACRYLATE | 0.250000 |
| DEA-CETYL PHOSPHATE | 0.200000 |
| SQUALANE | 0.200000 |
| BEHENYL ALCOHOL | 0.150000 |
| CETYL ALCOHOL | 0.150000 |
| ISOSTEARYL LINOLEATE | 0.150000 |
| LAURYL ALCOHOL | 0.150000 |
| LECITHIN | 0.150000 |
| MYRISTYL ALCOHOL | 0.150000 |
| PALMITIC ACID | 0.150000 |
| PETROLATUM | 0.150000 |
| STEARYL ALCOHOL | 0.150000 |
| HECTORITE | 0.100000 |
| HYDROGENATED POLYDECENE | 0.100000 |
| MAGNESIUM ALUMINUM SILICATE | 0.100000 |
| *OLEA EUROPAEA* (OLIVE) FRUIT OIL | 0.100000 |
| PEG-100 STEARATE | 0.100000 |
| PEG-12 DIMETHICONE | 0.100000 |
| POLYSORBATE 20 | 0.100000 |
| PROPYLENE GLYCOL | 0.100000 |
| STEARETH-20 | 0.100000 |
| TETRASODIUM EDTA | 0.100000 |
| TRIDECETH-6 | 0.100000 |
| *LAVANDULA ANGUSTIFOLIA* (LAVENDER) OIL | 0.060000 |
| ACRYLATES/CARBAMATE COPOLYMER | 0.050000 |
| DISODIUM LAURIMINODIPROPIONATE TOCOPHERYL PHOSPHATES | 0.050000 |
| SORBIC ACID | 0.050000 |
| SODIUM HYALURONATE | 0.033000 |
| CYCLODEXTRIN | 0.020000 |
| PENTASODIUM PENTETATE | 0.020000 |
| PHYTIC ACID | 0.020000 |
| POTASSIUM CITRATE | 0.020000 |
| POTASSIUM GLUCONATE | 0.020000 |
| RETINOL | 0.020000 |
| *SOLANUM LYCOPERSICUM* (TOMATO) FRUIT/LEAF/STEM EXTRACT | 0.020000 |
| ASCORBYL PALMITATE | 0.010000 |
| CERAMIDE 2 | 0.010000 |
| COPPER PCA | 0.010000 |
| *EMBLICA OFFICINALIS* FRUIT EXTRACT | 0.010000 |
| MICA | 0.010000 |
| PHOSPHOLIPIDS | 0.010000 |
| *PRUNUS AMYGDALUS DULCIS* (SWEET ALMOND) OIL | 0.010000 |
| RETINYL PALMITATE | 0.010000 |
| SOY ISOFLAVONES | 0.010000 |
| TITANIUM DIOXIDE (CI 77891) | 0.010000 |
| TOCOPHERYL ACETATE | 0.010000 |
| UBIQUINONE | 0.010000 |
| ZINC PCA | 0.010000 |
| AMINOBUTYRIC ACID | 0.001000 |
| PALMITOYL TETRAPEPTIDE-3 | 0.000002 |
| | 100% |

The present invention also provides a skin care product having the components listed in the following table.

| COMPONENTS | % (w/w) |
|---|---|
| WATER (AQUA) | 10 to 95 |
| SODIUM POLYACRYLATE | 0 to 5 |
| DIMETHICONE | 0 to 5 |
| CYCLOPENTASILOXANE | 0 to 5 |
| 1-METHYLHYDANTOINE-2-IMIDE | 0 to 5 |
| ARBUTIN | 0 to 5 |
| *CAMELLIA SINENSIS* LEAF EXTRACT | 0 to 5 |

-continued

| COMPONENTS | % (w/w) |
|---|---|
| RETINOL | 0 to 5 |
| BUTYLENE GLYCOL | 0 to 5 |
| CAPRYLIC/CAPRIC TRIGLYCERIDE | 0 to 5 |
| SILICA DIMETHYL SILYLATE | 0 to 5 |
| GLYCERYL OLEATE | 0 to 5 |
| QUERCETIN CAPRYLATE | 0 to 5 |
| *PUERARIA LOBATA* ROOT EXTRACT | 0 to 5 |
| *ARCTOSTAPHYLOS UVA URSI* LEAF EXTRACT | 0 to 5 |
| *SALIX ALBA* (WILLOW) BARK EXTRACT | 0 to 5 |
| PHOSPHOLIPIDS | 0 to 5 |
| ASCORBYL PALMITATE | 0 to 5 |
| RETINYL PALMITATE | 0 to 5 |
| TOCOPHERYL ACETATE | 0 to 5 |
| PENTASODIUM PENTETATE | 0 to 5 |
| CYCLODEXTRIN | 0 to 5 |
| POTASSIUM CITRATE | 0 to 5 |
| POTASSIUM GLUCONATE | 0 to 5 |
| PHYTIC ACID | 0 to 5 |
| SACCHAROMYCES/XYLINUM BLACK TEA FERMENT | 0 to 5 |
| DIACETYL BOLDINE | 0 to 5 |
| TRIDECETH-6 | 0 to 5 |
| PEG/PPG-18/18 DIMETHICONE | 0 to 5 |
| MICA | 0 to 5 |
| POLYMETHYL METHACRYLATE | 0 to 5 |
| METHYLPARABEN | 0 to 5 |
| TETRASODIUM EDTA | 0 to 5 |
| BENZYL ALCOHOL | 0 to 5 |
| DISODIUM EDTA | 0 to 5 |

The present invention also provides a skin care product having the components listed in the following table.

| COMPONENTS | % (w/w) |
|---|---|
| WATER (AQUA) | 92.930000 |
| SODIUM POLYACRYLATE | 0.300000 |
| DIMETHICONE | 1.000000 |
| CYCLOPENTASILOXANE | 1.000000 |
| 1-METHYLHYDANTOINE-2-IMIDE | 1.000000 |
| ARBUTIN | 0.100000 |
| *CAMELLIA SINENSIS* LEAF EXTRACT | 0.100000 |
| RETINOL | 0.100000 |
| BUTYLENE GLYCOL | 0.100000 |
| CAPRYLIC/CAPRIC TRIGLYCERIDE | 0.100000 |
| SILICA DIMETHYL SILYLATE | 0.010000 |
| GLYCERYL OLEATE | 0.010000 |
| QUERCETIN CAPRYLATE | 0.010000 |
| *PUERARIA LOBATA* ROOT EXTRACT | 0.010000 |
| *ARCTOSTAPHYLOS UVA URSI* LEAF EXTRACT | 0.100000 |
| *SALIX ALBA* (WILLOW) BARK EXTRACT | 0.250000 |
| PHOSPHOLIPIDS | 0.100000 |
| ASCORBYL PALMITATE | 0.100000 |
| RETINYL PALMITATE | 0.100000 |
| TOCOPHERYL ACETATE | 0.100000 |
| PENTASODIUM PENTETATE | 0.020000 |
| CYCLODEXTRIN | 0.020000 |
| POTASSIUM CITRATE | 0.020000 |
| POTASSIUM GLUCONATE | 0.020000 |
| PHYTIC ACID | 0.020000 |
| SACCHAROMYCES/XYLINUM BLACK TEA FERMENT | 0.250000 |
| DIACETYL BOLDINE | 0.010000 |
| TRIDECETH-6 | 0.100000 |
| PEG/PPG-18/18 DIMETHICONE | 1.000000 |
| MICA | 0.100000 |
| POLYMETHYL METHACRYLATE | 0.500000 |
| METHYLPARABEN | 0.100000 |
| TETRASODIUM EDTA | 0.020000 |
| BENZYL ALCOHOL | 0.200000 |
| DISODIUM EDTA | 0.100000 |

The present invention also provides a skin care product having the components listed in the following table.

| COMPONENTS | % (w/w) |
|---|---|
| WATER (AQUA) | 5 to 95 |
| BISABOLOL | 1 to 20 |
| *CAMELLIA SINENSIS* LEAF EXTRACT | 0 to 10 |
| *CUCUMIS SATIVUS* (CUCUMBER) FRUIT EXTRACT | 0 to 10 |
| CYCLOPENTASILOXANE | 0 to 10 |
| DIMETHICONE | 0 to 10 |
| *GLYCYRRHIZA GLABRA* (LICORICE) ROOT EXTRACT | 0 to 10 |
| PEG/PPG-18/18 DIMETHICONE | 0 to 10 |
| DIPOTASSIUM GLYCYRRHIZINATE | 0 to 5 |
| SODIUM POLYACRYLATE | 0 to 5 |
| BENZYL ALCOHOL | 0 to 5 |
| DISODIUM EDTA | 0 to 5 |
| *HAMAMELIS VIRGINIANA* (WITCH HAZEL) LEAF EXTRACT | 0 to 5 |
| METHYLPARABEN | 0 to 5 |
| *RANUNCULUS FICARIA* EXTRACT | 0 to 5 |
| TETRASODIUM EDTA | 0 to 5 |
| TRIDECETH-6 | 0 to 5 |
| CYCLODEXTRIN | 0 to 5 |
| PENTASODIUM PENTETATE | 0 to 5 |
| PHYTIC ACID | 0 to 5 |
| POTASSIUM CITRATE | 0 to 5 |
| POTASSIUM GLUCONATE | 0 to 5 |
| *SILYBUM MARIANUM* FRUIT EXTRACT | 0 to 5 |
| | 100% |

The present invention also provides a skin care product having the components listed in the following table.

| COMPONENTS | % (w/w) |
|---|---|
| WATER (AQUA) | 87.130000 |
| BISABOLOL | 5.000000 |
| *CAMELLIA SINENSIS* LEAF EXTRACT | 1.000000 |
| *CUCUMIS SATIVUS* (CUCUMBER) FRUIT EXTRACT | 1.000000 |
| CYCLOPENTASILOXANE | 1.000000 |
| DIMETHICONE | 1.000000 |
| *GLYCYRRHIZA GLABRA* (LICORICE) ROOT EXTRACT | 1.000000 |
| PEG/PPG-18/18 DIMETHICONE | 1.000000 |
| DIPOTASSIUM GLYCYRRHIZINATE | 0.500000 |
| SODIUM POLYACRYLATE | 0.450000 |
| BENZYL ALCOHOL | 0.200000 |
| DISODIUM EDTA | 0.100000 |
| *HAMAMELIS VIRGINIANA* (WITCH HAZEL) LEAF EXTRACT | 0.100000 |
| METHYLPARABEN | 0.100000 |
| *RANUNCULUS FICARIA* EXTRACT | 0.100000 |
| TETRASODIUM EDTA | 0.100000 |
| TRIDECETH-6 | 0.100000 |
| CYCLODEXTRIN | 0.020000 |
| PENTASODIUM PENTETATE | 0.020000 |
| PHYTIC ACID | 0.020000 |
| POTASSIUM CITRATE | 0.020000 |
| POTASSIUM GLUCONATE | 0.020000 |
| *SILYBUM MARIANUM* FRUIT EXTRACT | 0.020000 |
| | 100% |

The present invention also provides a skin care product having the components listed in the following table.

| COMPONENTS | % (w/w) |
|---|---|
| PURIFIED WATER (AQUA PURIFICATA) | 1 to 90 |
| PENTYLENE GLYCOL | 0 to 20 |
| KAOLIN | 0 to 20 |
| BENTONITE | 0 to 20 |
| SORBITAN STEARATE | 0 to 10 |
| COLLOIDAL SULFUR | 0 to 10 |
| TITANIUM DIOXIDE (CI 77891) | 0 to 10 |
| C12-15 ALKYL ETHYLHEXANOATE | 0 to 10 |
| MAGNESIUM ALUMINUM SILICATE | 0 to 10 |

-continued

| COMPONENTS | % (w/w) |
|---|---|
| GLYCERYL STEARATE | 0 to 10 |
| SODIUM DIHYDROXYCETYL PHOSPHATE | 0 to 10 |
| PEG-40 STEARATE | 0 to 10 |
| CAPRYLYL GLYCOL | 0 to 5 |
| PHENOXYETHANOL | 0 to 5 |
| TETRASODIUM EDTA | 0 to 5 |
| XANTHAN GUM | 0 to 5 |
| BISABOLOL | 0 to 5 |
| *EPILOBIUM ANGUSTIFOLIUM* FLOWER/LEAF/STEM EXTRACT | 0 to 5 |
| FARNESOL | 0 to 5 |
| PEG-150 DISTEARATE | 0 to 5 |
| IRON OXIDES (CI 77491, CI 77492, CI 77499) | 0 to 5 |
| PHYTIC ACID | 0 to 5 |
| POTASSIUM SORBATE | 0 to 5 |
| BUTYLENE GLYCOL | 0 to 5 |
| CAPRYLIC/CAPRIC TRIGLYCERIDE | 0 to 5 |
| HEXYLENE GLYCOL | 0 to 5 |
| MENTHOL | 0 to 5 |
| SODIUM GLUCONATE | 0 to 5 |
| GLYCERIN | 0 to 5 |
| *CAMELLIA SINENSIS* LEAF EXTRACT | 0 to 5 |
| *PUERARIA LOBATA* ROOT EXTRACT | 0 to 5 |
| SILICA DIMETHYL SILYLATE | 0 to 5 |
| GLYCERYL OLEATE | 0 to 5 |
| QUERCETIN CAPRYLATE | 0 to 5 |
| | 100% |

The present invention also provides a skin care product having the components listed in the following table.

| COMPONENTS | % (w/w) |
|---|---|
| PURIFIED WATER (AQUA PURIFICATA) | 61.2300 |
| PENTYLENE GLYCOL | 5.0000 |
| KAOLIN | 4.5000 |
| BENTONITE | 4.0000 |
| SORBITAN STEARATE | 3.5000 |
| COLLOIDAL SULFUR | 3.2500 |
| TITANIUM DIOXIDE (CI 77891) | 3.2500 |
| C12-15 ALKYL ETHYLHEXANOATE | 3.0000 |
| MAGNESIUM ALUMINUM SILICATE | 2.3500 |
| GLYCERYL STEARATE | 2.2500 |
| SODIUM DIHYDROXYCETYL PHOSPHATE | 2.0000 |
| PEG-40 STEARATE | 1.2000 |
| CAPRYLYL GLYCOL | 0.6000 |
| PHENOXYETHANOL | 0.4800 |
| TETRASODIUM EDTA | 0.4000 |
| XANTHAN GUM | 0.3500 |
| BISABOLOL | 0.3000 |
| *EPILOBIUM ANGUSTIFOLIUM* FLOWER/LEAF/STEM EXTRACT | 0.3000 |
| FARNESOL | 0.3000 |
| PEG-150 DISTEARATE | 0.3000 |
| IRON OXIDES (CI 77491, CI 77492, CI 77499) | 0.2000 |
| PHYTIC ACID | 0.2000 |
| POTASSIUM SORBATE | 0.2000 |
| BUTYLENE GLYCOL | 0.1600 |
| CAPRYLIC/CAPRIC TRIGLYCERIDE | 0.1600 |
| HEXYLENE GLYCOL | 0.1200 |
| MENTHOL | 0.1000 |
| SODIUM GLUCONATE | 0.1000 |
| GLYCERIN | 0.0800 |
| *CAMELLIA SINENSIS* LEAF EXTRACT | 0.0400 |
| *PUERARIA LOBATA* ROOT EXTRACT | 0.0400 |
| SILICA DIMETHYL SILYLATE | 0.0200 |
| GLYCERYL OLEATE | 0.0192 |
| QUERCETIN CAPRYLATE | 0.0008 |
| | 100% |

The present invention also provides a skin care product having the components listed in the following table.

| COMPONENTS | % (w/w) |
|---|---|
| PURIFIED WATER (AQUA PURIFICATA) | 0.612300 |
| PENTYLENE GLYCOL | 0.050000 |
| KAOLIN | 0.045000 |
| BENTONITE | 0.040000 |
| SORBITAN STEARATE | 0.035000 |
| COLLOIDAL SULFUR | 0.032500 |
| TITANIUM DIOXIDE (CI 77891) | 0.032500 |
| C12-15 ALKYL ETHYLHEXANOATE | 0.030000 |
| MAGNESIUM ALUMINUM SILICATE | 0.023500 |
| GLYCERYL STEARATE | 0.022500 |
| SODIUM DIHYDROXYCETYL PHOSPHATE | 0.020000 |
| PEG-40 STEARATE | 0.012000 |
| CAPRYLYL GLYCOL | 0.006000 |
| PHENOXYETHANOL | 0.004800 |
| TETRASODIUM EDTA | 0.004000 |
| XANTHAN GUM | 0.003500 |
| BISABOLOL | 0.003000 |
| *EPILOBIUM ANGUSTIFOLIUM* FLOWER/LEAF/STEM EXTRACT | 0.003000 |
| FARNESOL | 0.003000 |
| PEG-150 DISTEARATE | 0.003000 |
| IRON OXIDES (CI 77491, CI 77492, CI 77499) | 0.002000 |
| PHYTIC ACID | 0.002000 |
| POTASSIUM SORBATE | 0.002000 |
| BUTYLENE GLYCOL | 0.001600 |
| CAPRYLIC/CAPRIC TRIGLYCERIDE | 0.001600 |
| HEXYLENE GLYCOL | 0.001200 |
| MENTHOL | 0.001000 |
| SODIUM GLUCONATE | 0.001000 |
| GLYCERIN | 0.000800 |
| *CAMELLIA SINENSIS* LEAF EXTRACT | 0.000400 |
| *PUERARIA LOBATA* ROOT EXTRACT | 0.000400 |
| SILICA DIMETHYL SILYLATE | 0.000200 |
| GLYCERYL OLEATE | 0.000192 |
| QUERCETIN CAPRYLATE | 0.000008 |
| | 100% |

The invention claimed is:

1. A skin care product comprising:
   (I) at least two chelators comprising pentasodium pentetate and sodium gluconate; and
   (II) at least one skin care ingredient comprising arctostaphylos (*Uva ursi* leaf extract), and inhiphase (*Pueraria lobata* root extract).

2. The skin care product of claim 1, further comprising at least one chelator selected from ethylene diaminetetraacetic acid (EDTA), EDTA disodium salt, EDTA trisodium salt and EDTA tetrasodium salt.

3. The skin care product of claim 1, wherein the at least two chelators further comprise a chelator selected from cyclodextrin, phytic acid, potassium citrate, sodium citrate and potassium gluconate.

4. The skin care product of claim 1, wherein the at least one skin care ingredient further comprises a skin care ingredient selected from alpha-arbutin, hesperidin methyl chalcone, *Glycyrrhiza glabra* (licorice) root extract, *Glycine soja* (soybean) oil, quercetin caprylate, and a mixture of linoleic acid and at least one water soluble ester of ascorbic acid.

5. The skin care product of claim 1, wherein the at least one skin care ingredient further comprises a mixture of linoleic acid and at least one water soluble ester of ascorbic acid.

6. The skin care product of claim 5, wherein the water soluble ester of ascorbic acid is selected from the group consisting of sodium ascorbyl phosphate, potassium ascorbyl phosphate, magnesium ascorbyl phosphate and calcium ascorbyl phosphate.

7. The skin care product of claim 1, wherein the at least one skin care ingredient further comprises a skin care ingredient selected from substances that can increase collagen levels selected from dimethyl sulfone, silymarin and grape (*Vitis vinifera*) seed extract.

8. The skin care product of claim 1, wherein the at least one skin care ingredient further comprises a skin care ingredient selected from diacetyl boldine, arbutin, Tego cosmo, and sulfur.

9. The skin care product of claim 1, wherein the at least one skin care ingredient further comprises sulfur.

10. The skin care product of claim 9, wherein the sulfur is at about 1 weight % to about 6.5 weight %.

11. The skin care product of claim 1, wherein the at least one skin care ingredient further comprises a skin care ingredient selected from quercetin caprylate, bisabolol and silymarin (*Silybum marianum* fruit extract).

12. The skin care product of claim 1, wherein the at least one skin care ingredient further comprises a skin care ingredient selected from substances that can soothe the skin or reduce skin redness, wherein the substances are selected from licorice (*Glycyrrhiza glabra*) root extract, bisabolol, quercetin caprylate, dipotassium glycyrrhizinate and gatuline (*Ranunculus ficaria* extract).

13. The skin care product of claim 1, wherein the at least one skin care ingredient further comprises a skin care ingredient selected from skin conditioners, wherein the skin conditioners are selected from aminobutyric acid, bisabolol, *Centella asiatica* extract, *Solanum lycopersicum* (tomato) fruit/leaf/stem extract, jojoba *Simmondsia chinensis* (jojoba) seed oil, *Epilobium angustifolium* flower/leaf/stem extract, tribehenin, chrysin, N-hydroxysuccinimide, phytonadione, oxido reductase and dipeptide-2.

14. The skin care product of claim 1, wherein the at least one skin care ingredient further comprises a skin care ingredient selected from plant-derived skin care agents or botanical skin care agents selected from *Daucus carona sativa* (carrot) root or its extract, *Arnica montana* flower extract, hydrolyzed rice bran protein, *Ricinus communis* (castor) seed oil, *Butyrospermum parkii* (shea butter), *Theobroma cacao* (cocoa) seed butter, *Solanum lycopersicum* (tomato) fruit/leaf/stem extract, *Vaccinium angustifolium* (blueberry) fruit extract, *Aloe barbadensis* leaf extract, *Punica granatum* (pomegranate) extract, *Salix alba* (willow) bark extract, *Citrus aurantium dulcis* (orange) fruit extract, *Citrus medica limonum* (lemon) fruit extract, *Hamamelis virginiana* (witch hazel) leaf extract, *Glycine soja* (soybean) germ extract, *Pyrus malus* (apple) fruit extract, *Vitis vinifera* (grape) seed extract, *Carthamus tinctorius* (safflower) seed oil, *Oryza sativa* (rice) bran wax, *Vaccinium macrocarpon* (cranberry) seed, *Vaccinium angustifolium* (blueberry) seed, *Origanum majorana* leaf oil, *Citrus aurantium amara* (bitter orange) peel oil, *Anthemis nobilis* flower oil, *Oryza sativa* (rice) bran oil, *Macadamia ternifolia* seed oil, *Laminaria digitata* extract, *Punica granatum* seed extract, *Carica papaya* (papaya) fruit extract, colloidal oatmeal, *Butyrospermum parkii* (shea butter) oil, *Citrus grandis* (grapefruit) peel oil, *Citrus aurantium dulcis* (orange) oil, *Citrus nobilis* (mandarin orange) oil, *Illicium verum* (anise) fruit/seed oil, *Vaccinium macrocarpon* (cranberry) fruit juice, jojoba esters, *Avena sativa* (oat) kernel protein, *Laminaria digitata*, *Citrus aurantium bergamia* (bergamot) fruit oil, *Eugenia caryophyllus* (clove) bud oil, *Coriandrum sativum* (coriander) oil, *Zingiber officinale* (ginger) root oil, *Citrus medica limonum* (lemon) peel oil, *Citrus aurantifolia* (lime) oil, *Litsea cubeba* fruit oil, *Myristica fragrans* (nutmeg) kernel oil, *Citrus aurantium dulcis* (orange) oil, *Lonicera caprifolium* (honeysuckle) flower extract, *Lonicera japonica* (honeysuckle) flower extract, *Rosmarinus officinalis* (rosemary) leaf oil, *Citrus aurantium dulcis* (orange) peel, *Melaleuca alternifolia* (tea tree) oil, *Fucus vesiculosus* (seaweed) extract, *Carica papaya* (papaya) extract, *Hamamelis virginiana* (witch hazel) water, *Cananga odorata* flower oil, *Coffee arabica* (coffee) seed extract, *Saccharomyces/Xylinum*/black tea ferment, *Glyzyrrhiza glabra* (licorice) root extract, *Citrus nobilis* (mandarin orange) fruit extract, *Citrullus vulgaris* (watermelon) fruit extract, caffeine, *Euterpe oleracea* (Acai) fruit extract and *Silybum marianum* fruit extract.

15. The skin care product of claim 1, wherein the at least one skin care ingredient further comprises a skin care ingredient selected from the group consisting of pearl powder, hexapeptide-10, hydrogenated castor oil, beeswax (*Cera alba*), allantoin, zinc oxide, isononyl isononanoate, isohexadecane, benzoic acid, bentonite, 1-methylhydantoin-2-imide, acrylates/carbamate copolymer, arbutin, lactic acid, mannitol, octoxynol-9, zinc salt of 1-pyrrolidone carboxylic acid, copper salt of 1-pyrrolidone carboxylic acid, sea salt, cocamidopropyl betaine, citric acid, malic acid, superoxide dismutase, jojoba esters, xanthan gum, caffeine, ectoin and ethylene brassylate.

16. The skin care product of claim 1, wherein the at least one skin care ingredient is present at up to 10% (w/w).

17. The skin care product of claim 16, wherein the at least one skin care ingredient is present at up to 5% (w/w).

18. The skin care product of claim 3, further comprising at least one enhancer selected from the group consisting of ethylene diaminetetraacetic acid (EDTA), EDTA disodium salt, EDTA trisodium salt and EDTA tetrasodium salt.

19. The skin care product of claim 3, further comprising EDTA disodium salt and EDTA tetrasodium salt.

20. The skin care product of claim 3, further comprising EDTA tetrasodium salt.

21. The skin care product of claim 1, further comprising a chelator selected from phytic acid, and potassium citrate.

22. The skin care product of claim 21, further comprising EDTA tetrasodium salt.

23. The skin care product of claim 1, further comprising EDTA tetrasodium salt.

24. The skin care product of claim 1, wherein each of the chelators is present at at least about 0.01% (w/w).

25. The skin care product of claim 1, wherein each of the chelators is present at a level ranging from about 0.01% to about 1% (w/w).

26. The skin care product of claim 25, wherein each of the chelators is present at a level ranging from about 0.02% to about 0.5% (w/w).

27. The skin care product of claim 1, wherein each of the chelators is present at up to 5% (w/w).

28. The skin care product of claim 1, wherein the total level of all the chelators combined ranges from about 0.05% to about 10%.

29. The skin care product of claim 28, wherein the total level of all the chelators combined ranges from about 0.1% to about 5%.

30. The skin care product of claim 1, further comprising at least one emollient/humectant/moisturizer.

31. The skin care product of claim 1, further comprising at least one active skin care agent other than the skin care ingredients recited in claim 1.

32. The skin care product of claim 31, wherein the at least one active skin care agent is selected from essential oils, antioxidants, free-radical scavengers, reducing agents, collagen stimulating agents, collagen promoters, soluble collagens, self tanners, anti-acne agents, anti-microbial agents, vitamins, skin protecting agents, skin bleaching agents, skin soothing agents, skin conditioners, skin healing agents, anti-redness agents, anti-swelling agents, depuffing agents, substances that can plump the skin and substances that can firm or tone the skin.

33. The skin care product of claim 11, further comprising at least one substance that can soothe the skin or reduce skin redness, wherein the at least one substance is selected from licorice (*Glycyrrhiza glabra*) root extract, bisabolol, quercetin caprylate, dipotassium glycyrrhizinate and gatuline (*Ranunculus ficaria* extract).

34. The skin care product of claim 11, further comprising at least one skin protecting agent against UV light.

35. The skin care product of claim 12, further comprising at least one skin protecting agent against UV light.

36. The skin care product of claim 33, further comprising at least one skin protecting agent against UV light.

37. A process of preparing the skin care product of claim 1, comprising mixing the at least two chelators and the at least one skin care ingredient to form the skin care product.

38. A method of caring for the skin of a subject, comprising applying the skin care product of claim 1 to the skin of the subject.

* * * * *